(12) United States Patent
Fayada

(10) Patent No.: US 11,039,862 B2
(45) Date of Patent: Jun. 22, 2021

(54) VERTEBRAL STABILISATION DEVICE

(71) Applicant: Paul Fayada, Mauzac (FR)

(72) Inventor: Paul Fayada, Mauzac (FR)

( * ) Notice: Subject to any disclaimer, the term of this patent is extended or adjusted under 35 U.S.C. 154(b) by 169 days.

(21) Appl. No.: 16/320,302

(22) PCT Filed: Jul. 24, 2017

(86) PCT No.: PCT/EP2017/068688
§ 371 (c)(1),
(2) Date: Jan. 24, 2019

(87) PCT Pub. No.: WO2018/019792
PCT Pub. Date: Feb. 1, 2018

(65) Prior Publication Data
US 2019/0269441 A1 Sep. 5, 2019

(30) Foreign Application Priority Data

Jul. 25, 2016 (FR) ...................................... 16 57131

(51) Int. Cl.
*A61B 17/70* (2006.01)

(52) U.S. Cl.
CPC ...... *A61B 17/7049* (2013.01); *A61B 17/7002* (2013.01); *A61B 17/7008* (2013.01); *A61B 17/7011* (2013.01); *A61B 17/7019* (2013.01); *A61B 17/7026* (2013.01); *A61B 17/7043* (2013.01); *A61B 2017/7073* (2013.01)

(58) Field of Classification Search
CPC ............ A61B 17/7001; A61B 17/7002; A61B 17/7004; A61B 17/7007; A61B 17/7008; A61B 17/7011; A61B 17/7013; A61B 17/7019; A61B 17/7026; A61B 17/7043; A61B 2017/7073
See application file for complete search history.

(56) References Cited

U.S. PATENT DOCUMENTS 5,375,823 A * 12/1994 Navas ................ A61B 17/7005
623/17.15
5,415,661 A * 5/1995 Holmes .............. A61B 17/7026
606/255
(Continued)

FOREIGN PATENT DOCUMENTS

DE 101 17 426 A1 10/2002

OTHER PUBLICATIONS

International Search Report of PCT/EP2017/068688 dated Sep. 25, 2017 [PCT/ISA/210].

*Primary Examiner* — Larry E Waggle, Jr.
(74) *Attorney, Agent, or Firm* — Sughrue Mion, PLLC

(57) ABSTRACT

A vertebral stabilisation device, consisting of at least two linking elements arranged to link two separate vertebrae together, and attachment elements for attaching the ends of each linking element to the two separate vertebrae, characterised in that the length of the linking elements and the arrangement of the attachment elements are such that each linking element can extend diagonally between the two vertebrae to which it is attached, intersecting the mean sagittal plane of the vertebral column, the two linking elements intersecting substantially at said plane, and in that at least the attachment elements situated on a same side of the mean sagittal plane of the vertebral column and on separate vertebrae are not attached to each other.

20 Claims, 12 Drawing Sheets

(56) References Cited

U.S. PATENT DOCUMENTS

| | | | |
|---|---|---|---|
| 7,601,166 B2* | 10/2009 | Biedermann | A61B 17/701 |
| | | | 606/255 |
| 2003/0163132 A1* | 8/2003 | Chin | A61B 17/7059 |
| | | | 606/280 |
| 2006/0089645 A1* | 4/2006 | Eckman | A61B 17/7011 |
| | | | 606/254 |
| 2006/0106381 A1* | 5/2006 | Ferree | A61B 17/025 |
| | | | 606/248 |
| 2008/0262550 A1* | 10/2008 | Ferree | A61B 17/70 |
| | | | 606/263 |
| 2010/0049254 A1 | 2/2010 | Biedermann et al. | |
| 2010/0094344 A1* | 4/2010 | Trieu | A61B 17/7011 |
| | | | 606/246 |
| 2011/0257685 A1* | 10/2011 | Hay | A61B 17/7011 |
| | | | 606/263 |

* cited by examiner

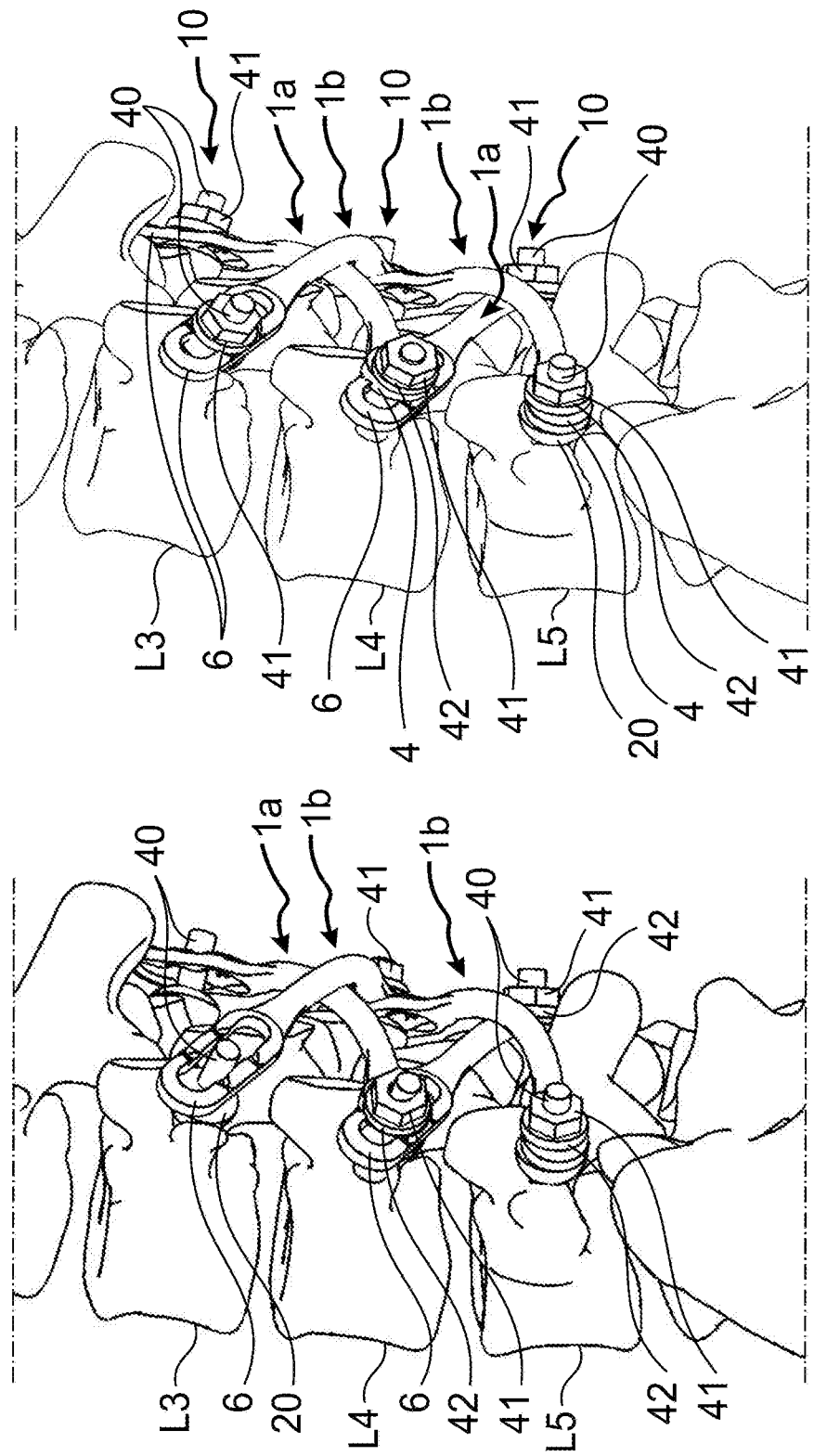

VERTEBRAL STABILISATION DEVICE

The present invention relates to the field of surgical implants and more particularly to vertebral stabilization devices that are implanted in the human body for treatment of diseases of the spine.

BACKGROUND ART

There are a great many vertebral stabilization devices, of which the common feature is that they are arranged to connect adjacent vertebrae by means of rods or bars that extend substantially on a plane parallel to the median sagittal plane of the vertebral column.

The stabilization obtained is then very effective but leads to a blocking of the movements of the vertebrae relative to each other. This blocking reduces the pain that the patient may feel, but it obviously affects the mobility of the patient to the point of being a handicap.

OBJECT OF THE INVENTION

It is an object of the invention to make available a means for stabilizing the vertebral column of a patient and/or for correcting a deformation between vertebrae of the vertebral column, by connecting two vertebrae to each other without completely blocking the relative movements of the vertebrae that are thus connected.

BRIEF DISCLOSURE OF THE INVENTION

To this end, a vertebral stabilization device is provided according to the invention, comprising at least two main linking elements arranged to connect two separate vertebrae to each other, and attachment elements for attaching the ends of each linking element to the two separate vertebrae. Each main linking element has a median plane containing a longitudinal direction of the main linking element. The main linking elements are of such a length, and the attachment elements are so arranged, that each main linking element can extend diagonally between the two vertebrae to which it is attached, intersecting the median sagittal plane of the vertebral column, the two main linking elements intersecting substantially at said median sagittal plane of the vertebral column. The device is arranged to permit a physiological angular clearance of the two vertebrae with respect to each other.

Thus, the two vertebrae are connected to each other by two linking elements, for example rods, which intersect substantially at the median sagittal plane of the vertebral column, and the device is arranged to permit a physiological angular clearance of the two vertebrae with respect to each other. This link is of course more flexible than a link afforded by rods that extend on a plane parallel to the median sagittal plane. Indeed, in the invention, the length of the linking elements is greater than in the case of rods extending on a plane parallel to the median sagittal plane, and their intersecting allows a stabilization structure to be obtained which is relatively deformable in the three spatial planes, particularly at the region of the intersection of the linking elements. This arrangement in fact permits a physiological clearance of the vertebral column in flexion in the median sagittal plane and in lateral inclination in the median frontal plane, and also in torsion around the spinal axis. The extent of this displacement, of a few degrees, is admittedly less than that of a non-stabilized vertebral column, but sufficient to improve substantially the comfort of the patients. It is possible, with the invention, to provide different modes of vertebral stabilization and corrections of deformations between vertebrae with respect to the physiological equilibrium by controlling the mobility of the instrumentation, and of the vertebrae equipped with the instrumentation, in the three spatial planes. Depending on the disease in question, it is thus possible, with the invention, to permit a greater or lesser angular clearance of the vertebrae with respect to each other. It is moreover possible to diagonally bridge two non-adjacent vertebrae.

The linking elements, thus arranged and positioned, at least partially reproduce an organic architecture, especially in terms of the histology of bone and disc and in terms of myology, which facilitates its incorporation in the body and its acceptance by the patient.

According to a first possible arrangement of the stabilization device, at least the attachment elements situated on a same side of the median sagittal plane of the vertebral column and on separate vertebrae are free with respect to each other.

This arrangement permits very substantial clearance of the vertebrae with respect to each other.

According to a second possible arrangement of the stabilization device, the device comprises, on each side of the median sagittal plane, a lateral linking element connecting two attachment elements to each other on the same side of the median sagittal plane, each lateral linking element being arranged to allow the attachment elements connected by it to move toward each other, and to limit a spacing apart of said attachment elements to a distance equal to the length of the lateral linking element.

This arrangement makes it possible to limit the maximum clearance of the vertebrae with respect to each other beyond the physiological clearance.

Other features and advantages of the invention will become clear on reading the following description of particular non-limiting embodiments of the invention.

BRIEF DESCRIPTION OF THE FIGURES

Reference will be made to the attached drawings, in which:

FIGS. 2 to 5 are views similar to FIG. 1 and illustrate the placement of vertebral stabilization devices according to a first embodiment of the invention, in a first arrangement of the device;

FIG. 6 is a schematic perspective view of the posterior part of this spine after placement of the vertebral stabilization devices according to the first embodiment;

DETAILED DESCRIPTION OF THE INVENTION

Figure 2:
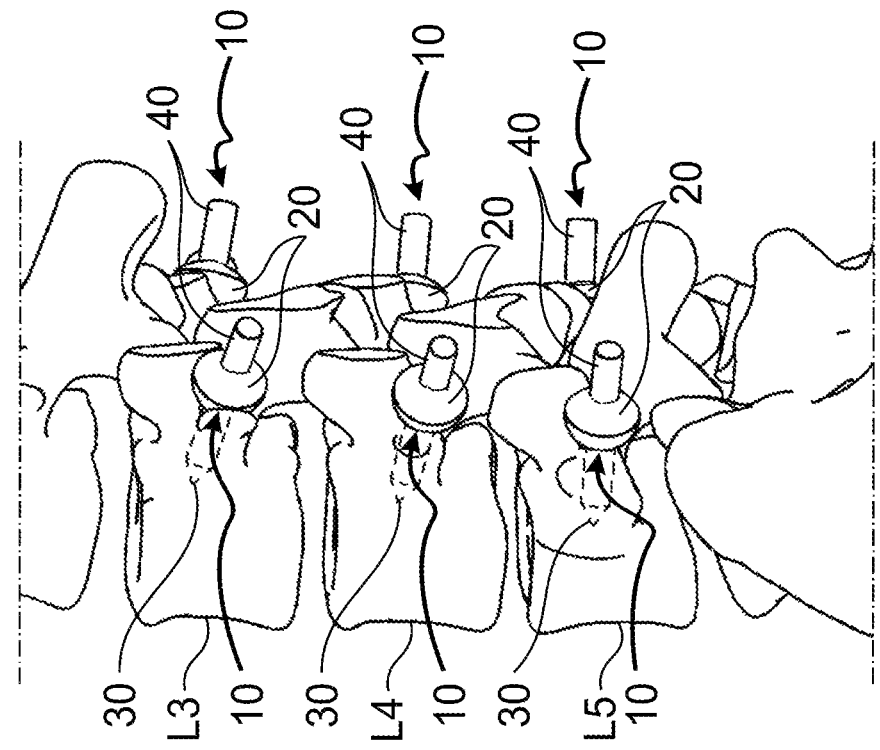

With reference to FIGS. 1 to 11, the vertebral stabilization device according to the first embodiment of the invention comprises pairs of rods 1, forming main linking elements, arranged to connect two separate vertebrae to each other, and attachment elements 10 for attaching the ends of each rod 1 to the two separate vertebrae.

Each rod 1 extends along a median longitudinal plane containing a longitudinal direction of the rod. The rods 1 have a length, measured in this longitudinal direction, which is such that each rod 1 can extend diagonally between the two vertebrae to which it is attached, intersecting the median sagittal plane S of the vertebral column, the two rods 1 of each pair of rods 1 intersecting substantially at said median sagittal plane S.

The rods 1 have a curved central portion 2 (the center of curvature being located substantially in the median longitudinal plane), an end portion 3 provided with a ring 4 of substantially circular shape, and an end portion 5 provided with an oblong loop 6 with a main axis extending in the continuation of the central axis of the end portion 5. The ring 4 and the oblong loop 6 extend along planes inclined with respect to each other.

The loop 6 has a first surface and second surface which are perpendicular to the axis of its opening and substantially plane. The first surface is intended to be oriented toward the vertebra. The edge delimiting the opening of the oblong loop 6 comprises, on the second surface, reinforcements 7 having a spherical cap shape and defining successive positions along the main axis of the loop 6.

Figure 9:
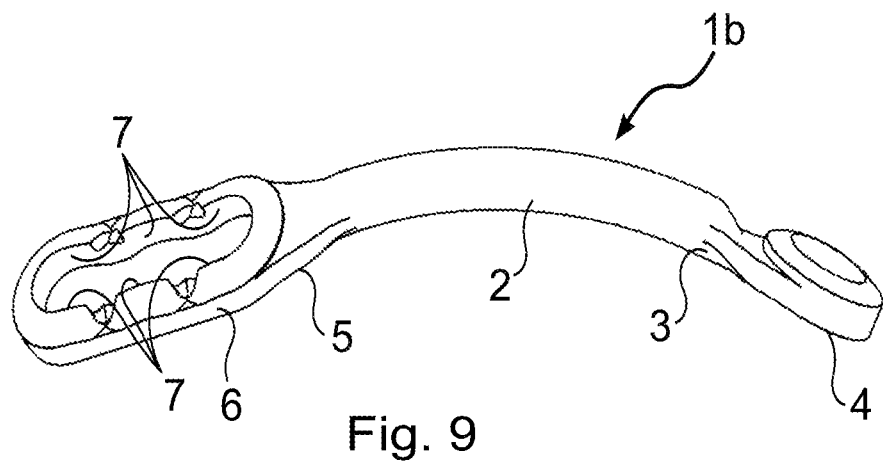
FIG. 9 is a schematic profile view of a second of the rods of one of these devices.
Figure 10:
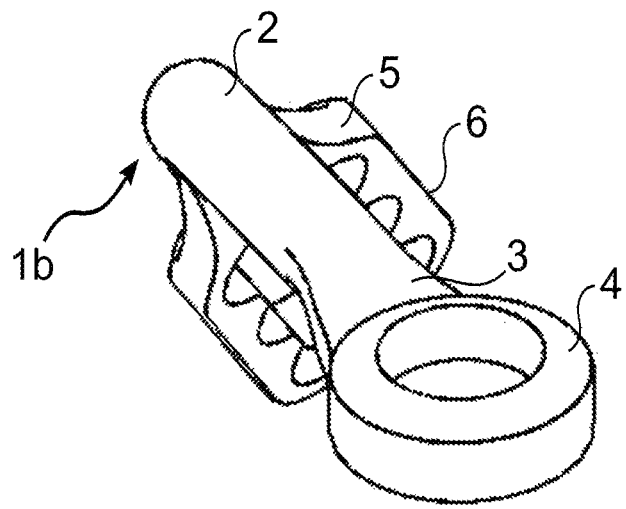
FIG. 10 is a schematic end view of this second rod.

Each pair of rods 1 comprises a rod 1 labeled 1a (shown more particularly in FIGS. 7 and 8) and a rod 1 labeled 1b (shown more particularly in FIGS. 9 and 10). The rods 1a and 1b have different radii of curvature: the central portion 2 of the rod 1a has a radius greater than the radius of the central portion 2 of the rod 1b.

The rods 1 are here made of organic material. For example, the rods 1 are made of a thermoplastic such as polyether ether ketone (PEEK).

In this way, the rods 1 ensure that the vertebral stabilization device is relatively deformable not only by virtue of their shape and their arrangement, but also by virtue of their material.

If necessary, in order to improve the mechanical properties of the rods 1 without increasing their diameter, it is possible to mix reinforcement fibers with the organic material.

Each attachment element 10 comprises a peg having a shouldered segment 20 which extends between a pedicle screw 30, and a threaded rod 40 coaxial to the pedicle screw 30. The threaded rod 40 is intended to cooperate with a nut 41 having a base 42.

The shouldered segment 20 comprises a first, spherical-cap-shaped surface on the side toward the pedicle screw 30 and a second, truncated surface on the side toward the threaded rod 40.

The ring 4 has a surface substantially in the shape of a concave spherical cap, for bearing on the second, truncated surface of the shouldered segment 20 or on the edges of the loop 6, and a surface substantially in the shape of a convex spherical cap, for cooperating with the base 42 of the nut 41.

Figure 1:
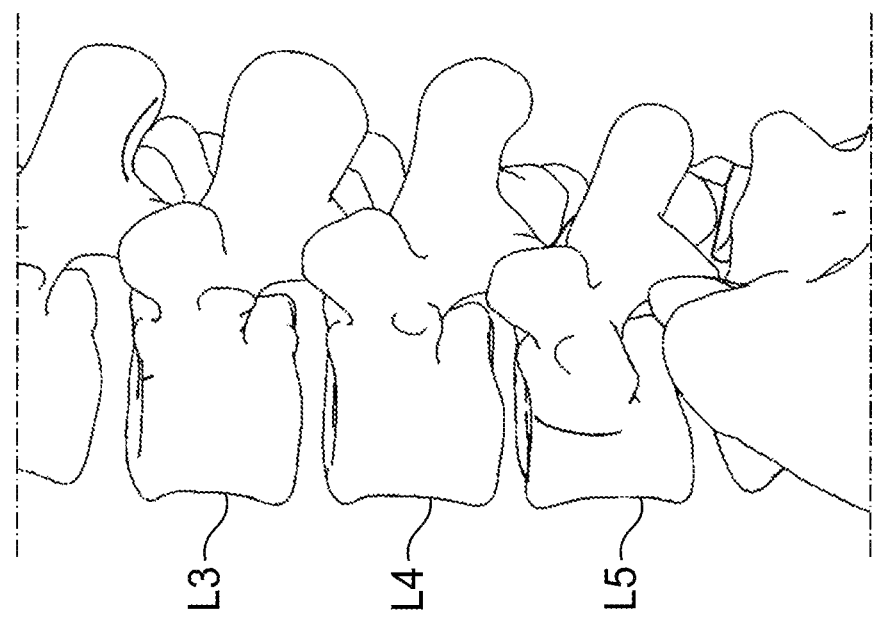
FIG. 1 is a schematic perspective view of the posterior part of a spine.

The stabilization device according to the invention is fitted in place, if necessary after partial or total removal of the spinous processes of the vertebrae concerned and optionally after partial milling of articular masses (FIG. 1 shows the spine prior to cutting of said processes). In FIGS. 2 to 6, it will be seen that the spinous processes of vertebrae L3 and L4 have been reduced: a first stabilization device will be installed between lumbar vertebrae L5, L4, and a second stabilization device will be installed between lumbar vertebrae L4, L3.

The placement of the stabilization devices commences by screwing pedicle screws 30 in order to fix the attachment elements 10 to the vertebrae concerned (FIG. 2).

The rods 1 will be fixed to the attachment elements 10 in such a way that each rod 1 extends diagonally between two adjacent vertebrae, intersecting the median sagittal plane S of the portion of the spine formed by vertebrae L5 to L3, the two rods 1 of each pair of rod 1 intersecting substantially at said plane S. The rods 1a are disposed closest to the vertebral column, and the rods 1b straddle the rods 1a.

Figure 3:
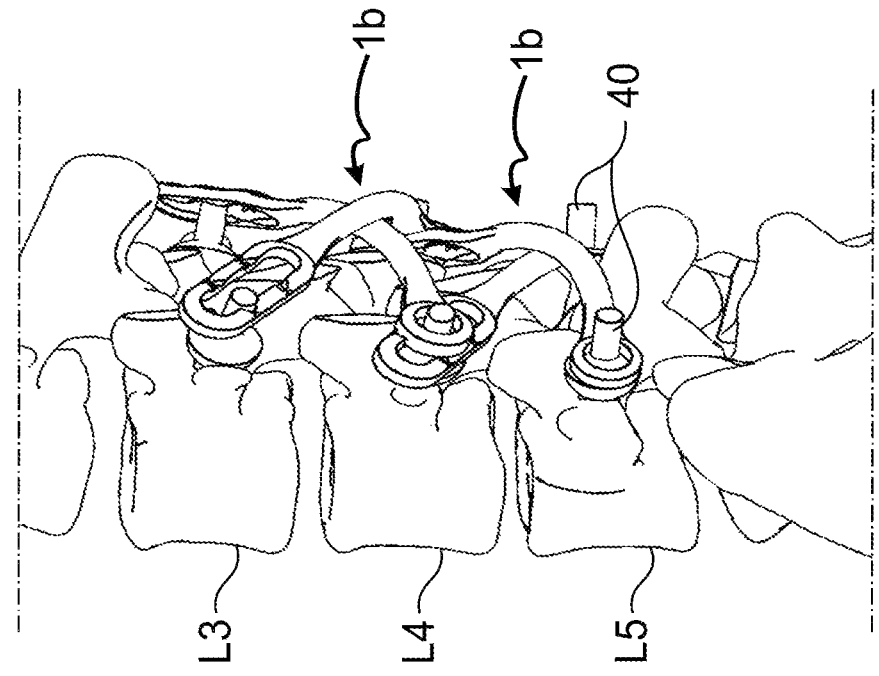

For the placement of the first stabilization device, the rings 4 of the rod 1a and of the rod 1b are engaged on the threaded rods 40 of the attachment elements 10 screwed into vertebra L5, and the oblong loops 6 of said rods 1a and 1b are engaged on the threaded rods 40 of the attachment elements 10 screwed into vertebra L4, in such a way that the rods 1a and 1b intersect (FIG. 3).

Figure 4:
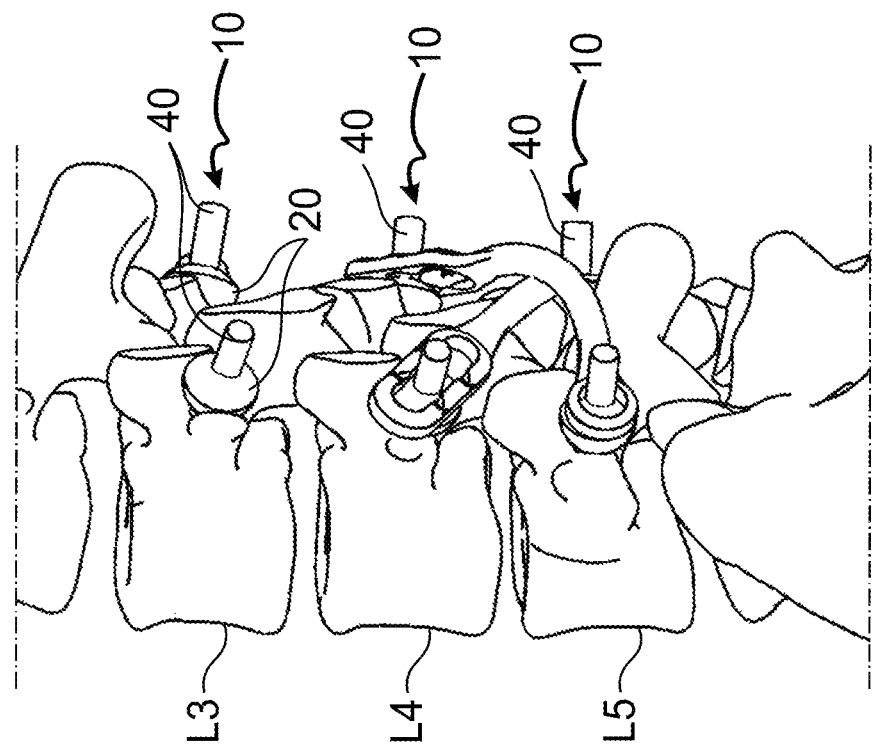
Figure 7:
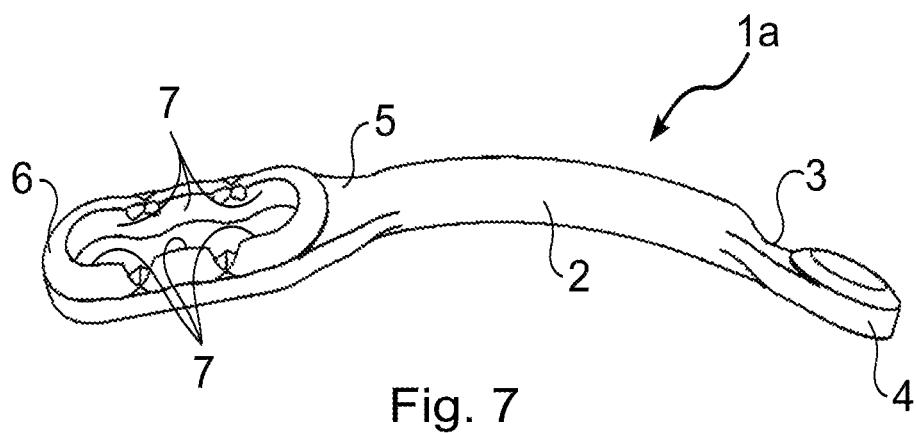
FIG. 7 is a schematic profile view of a first of the rods of one of these devices.
Figure 8:
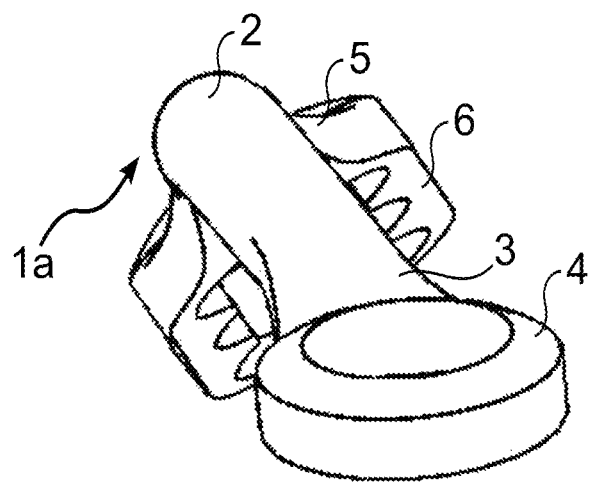
FIG. 8 is a schematic end view of this first rod.

For the placement of the second stabilization device, the rings 4 of the rod 1a and of the rod 1b are engaged on the threaded rods 40 of the attachment elements 10 screwed into vertebra L4 (that is to say over the oblong loops 6 of the rods 1a, 1b of the first stabilization device) and the oblong loops 6 of said rods 1a and 1b are engaged on the threaded rods 40 of the attachment elements 10 screwed into vertebra L3, in such a way that the rods 1a and 1b intersect (FIG. 4). The ring 4 of the rod 1a of the second stabilization device is engaged on the same threaded rod as the loop 6 of the rod 1a of the first stabilization device, and the ring 4 of the rod 1b of the second stabilization device is engaged on the same threaded rod as the loop 6 of the rod 1b of the first stabilization device.

The nuts 41 are then engaged on the threaded rods 40, and vertebrae L5 to L3 are correctly positioned and maintained in position with respect to each other before the nuts 41 are tightened in order to clamp the rings 4 and the oblong loops 6 against the second, truncated surface of the shouldered segments 20 (FIGS. 5 and 6).

The oblong loops 6 make it possible to set the tension of the rods 1a and 1b before they are tightened, by adjusting the position of the threaded rod 40 along the main axis of the oblong loop 6. This tensioning thus makes it possible to carry out possible correction of the positioning of the vertebrae relative to each other by combined or separate actions on one or both rods of one and the same vertebral segment.

It will be noted that, according to the first arrangement of the device, the attachment elements 10 situated on a same side of the median sagittal plane S of the vertebral column are free with respect to each other.

The rods 1 have mechanical properties allowing them to support forces of compression, traction, flexion and torsion, of the kind that normally occur during natural mobilization of the vertebral column.

In the variant of FIGS. 15 to 19, the ring 4 and the loop 6 of each rod 1a, 1b have plane faces.

A bushing 60 is lodged in the ring 4, said bushing 60 being provided at each of its ends with a flange 60.1 for covering the corresponding face of the ring 4. The flanges 60.1 provide a plane bearing and improve the hold of the rods 1a, 1b after the attachment elements 10 have been screwed in.

An interface 70 is engaged on the loop 6 of each rod 1a, 1b. The interface 70 comprises two plates 71, which are kept parallel to each other and at a distance from each other by an inclined spacer 72. The inclined spacer 72 has a relative elasticity allowing it to permit the plates 71 to move toward each other. The plates 71 extend on the faces of the loop 6 and have an orifice 73 passing through them in order to receive the threaded rod 40.

Each attachment element 10 comprises a peg having a shouldered segment 20 which extends between a pedicle screw 30 and a threaded rod 40 coaxial to the pedicle screw 30. The threaded rod 40 is intended to cooperate with a nut 41 having a base 42. The base 42 is plane, so as to be able to be pressed flat against a flange 60.1 or against a plate 71.

The shouldered segment 20 comprises a first, spherical-cap-shaped surface toward the pedicle screw 30, and a second, plane surface toward the threaded rod in order to serve as a plane bearing either for a flange 60.1 or for a plate 71.

It will be appreciated that the arrangement of the loops 6 and of the interfaces 70 allows the interface 70 to slide along the loop 60, permitting a large number of relative positions.

Figure 12:
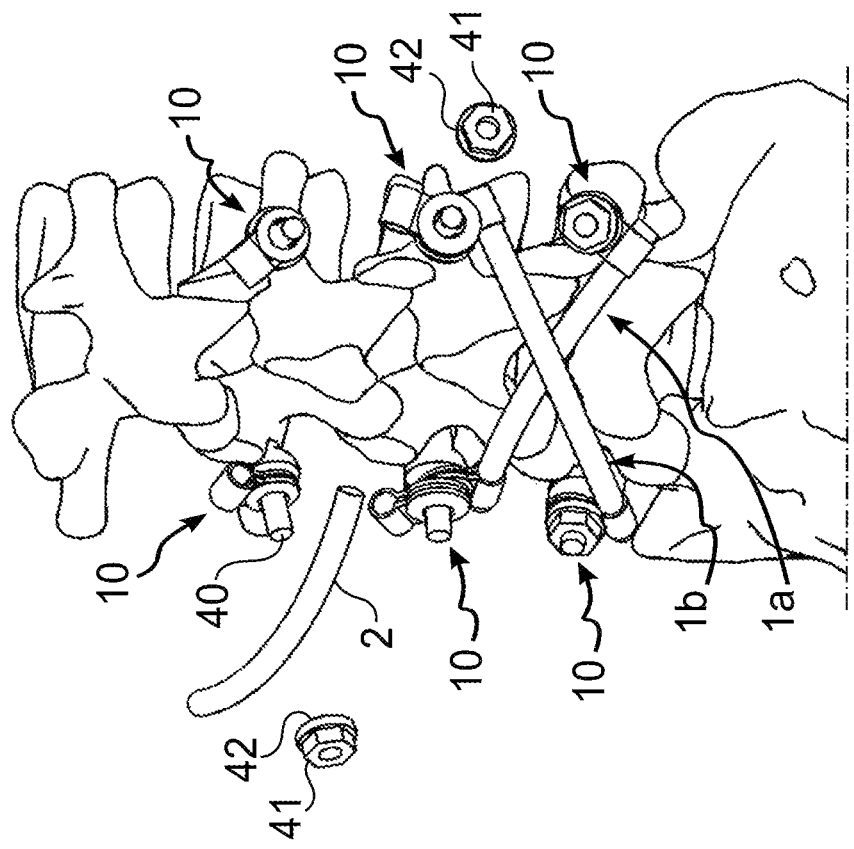
FIG. 12 is a schematic perspective view of the posterior part of a spine in the course of being equipped with vertebral stabilization devices according to a second embodiment of the invention, in the first arrangement of the device.
Figure 11:
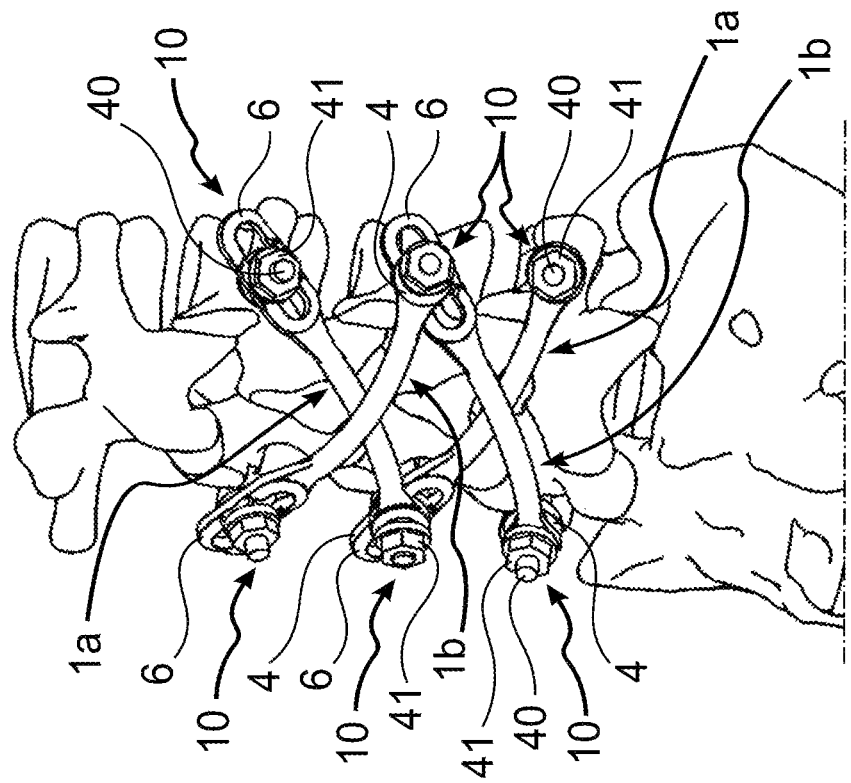
FIG. 11 is a schematic perspective view, at a viewing angle different than that of FIGS. 1 to 6, of the posterior part of the spine equipped with vertebral stabilization devices according to the first embodiment, in the first arrangement of the device.
Figure 14:
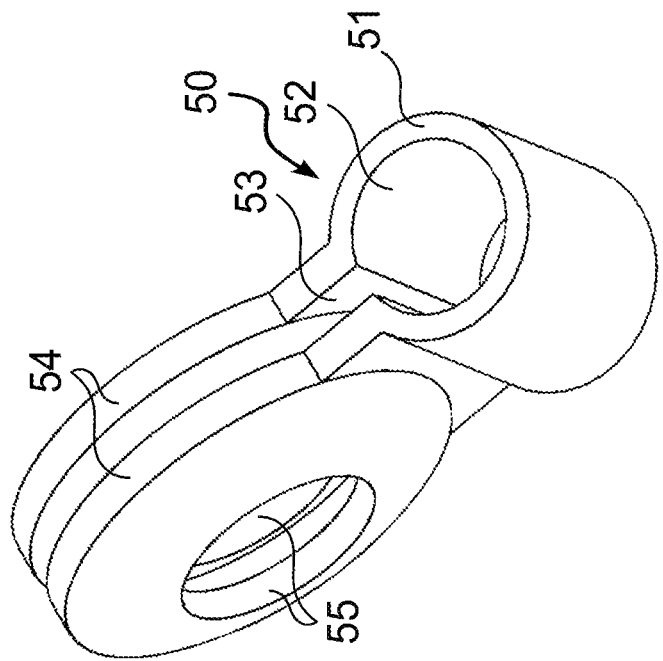
FIGS. 13 and 14 are schematic perspective views of attachment elements for the rods of these devices.
Figure 13:
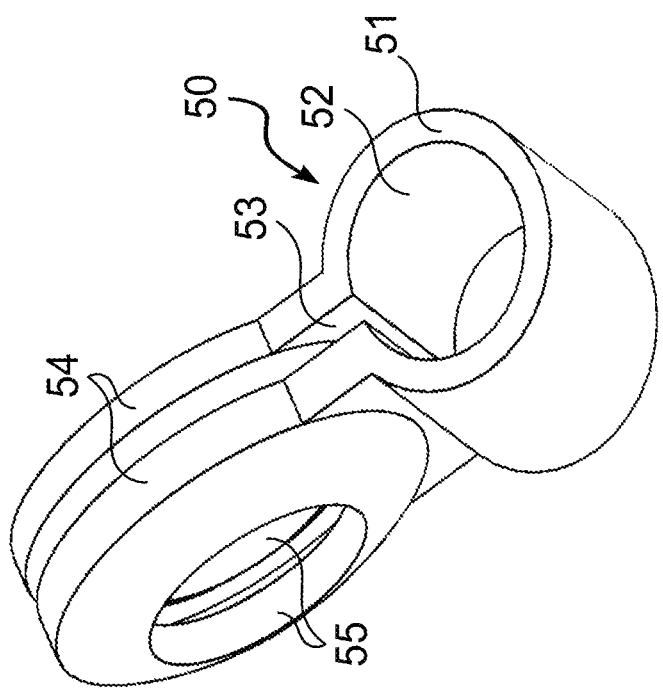
Figure 16:
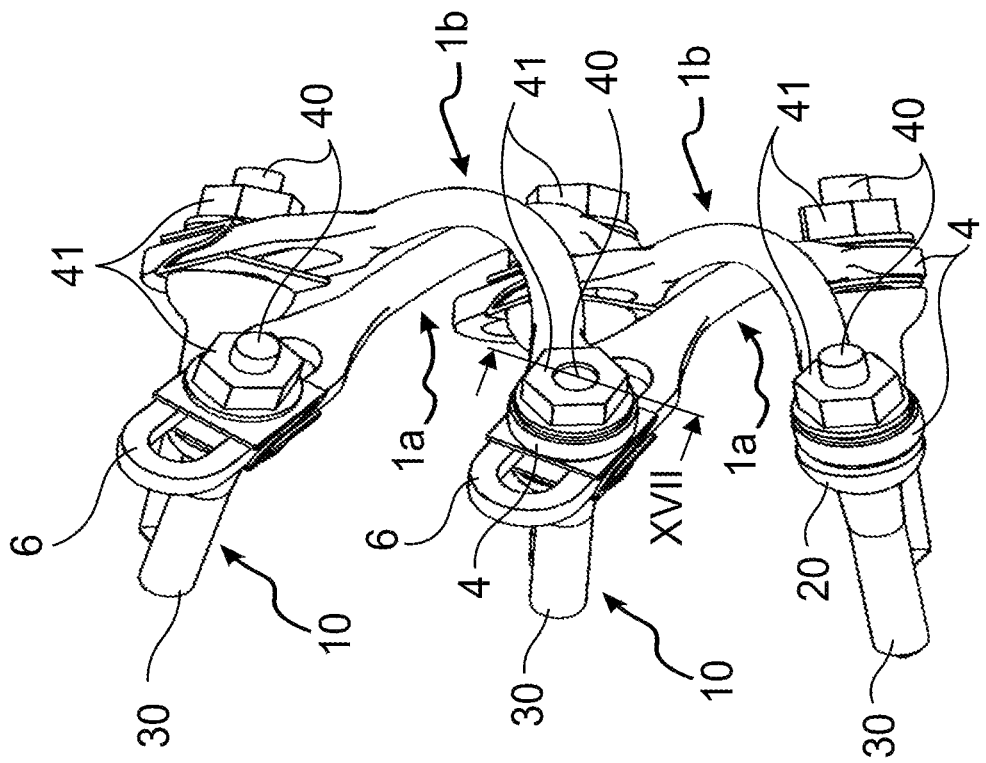
FIG. 16 is a perspective view of these stabilization devices.
Figure 15:
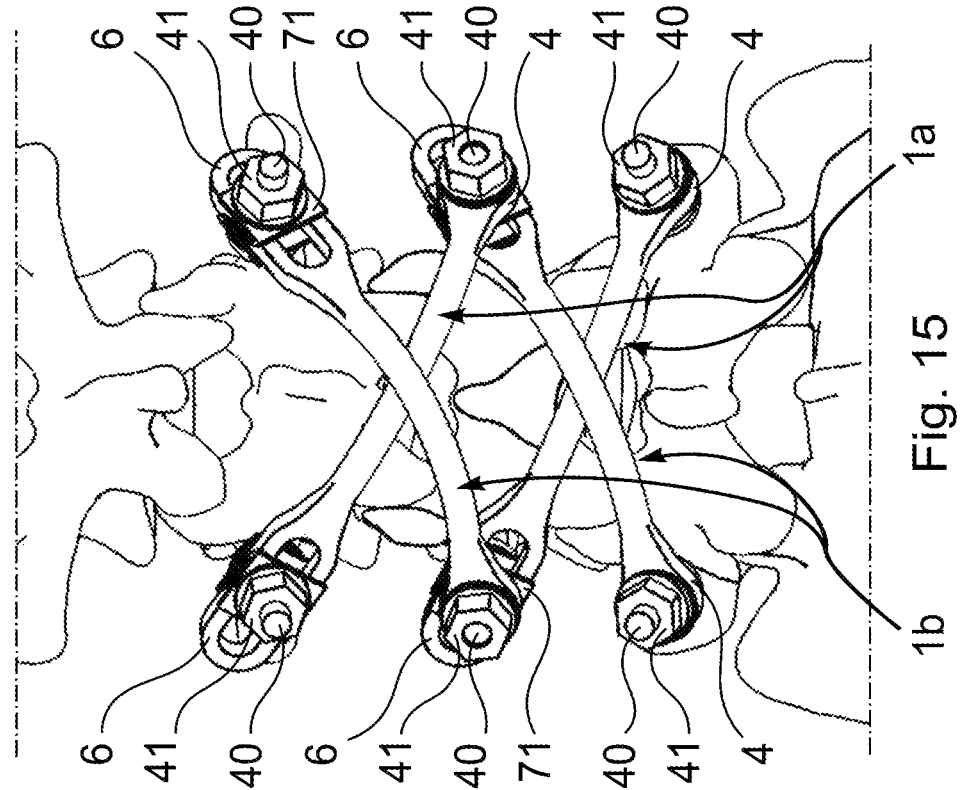
FIG. 15 is a view, similar to FIG. 11, of vertebral stabilization devices according to a variant of the first embodiment of the invention.
Figure 17:
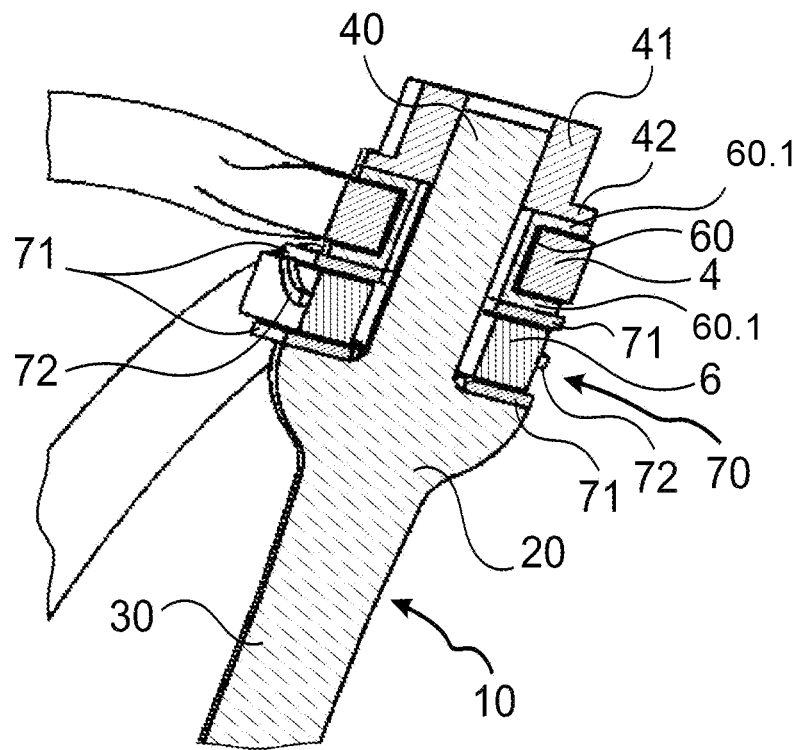
FIG. 17 is a detail view of one of these devices, in cross section along the plane XVII of FIG. 16.
Figure 18:
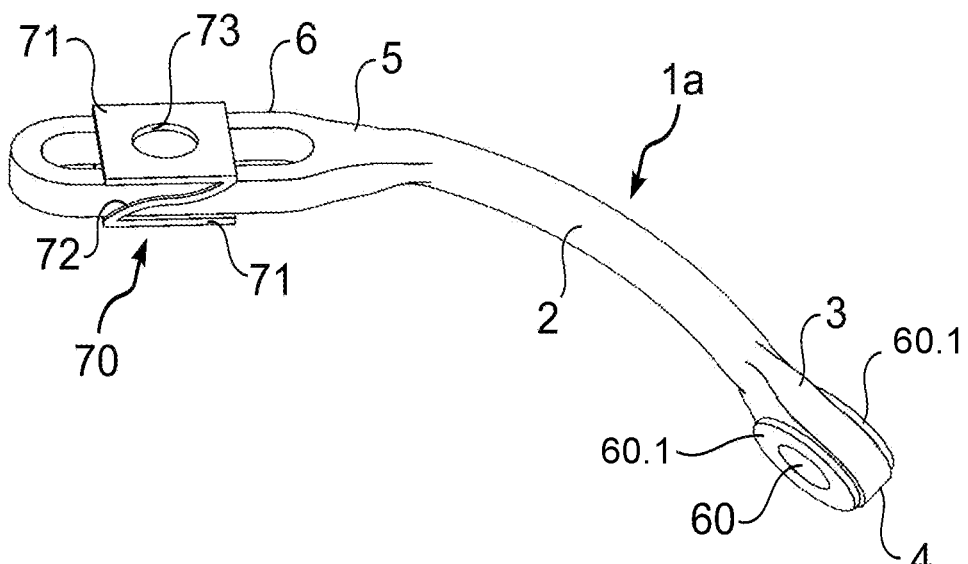
FIGS. 18 and 19 are views, similar to the views of FIGS. 7 and 9 respectively, of the first and second rods according to said variant of the first embodiment of the invention.
Figure 19:
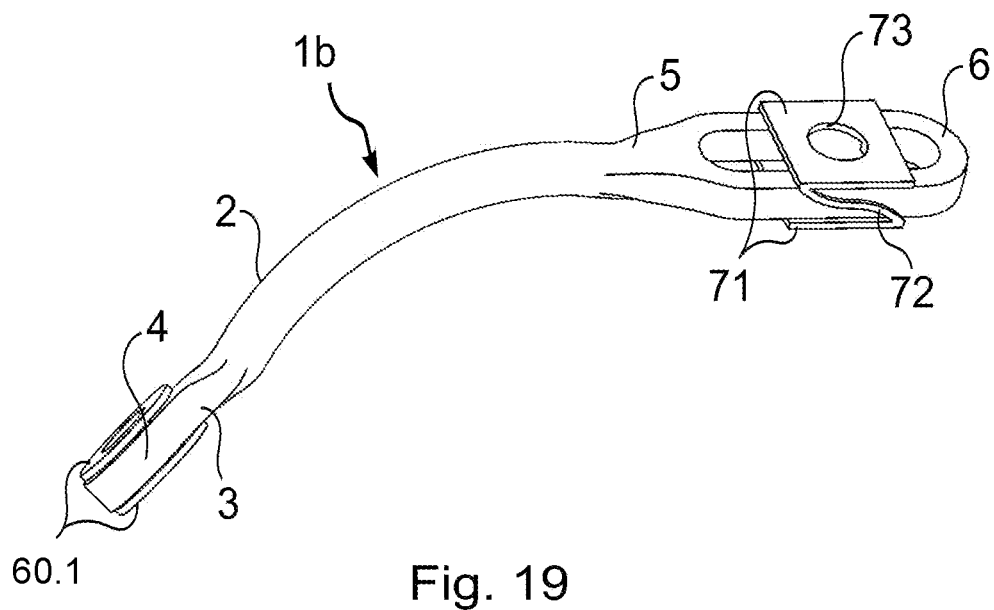
Figure 21:
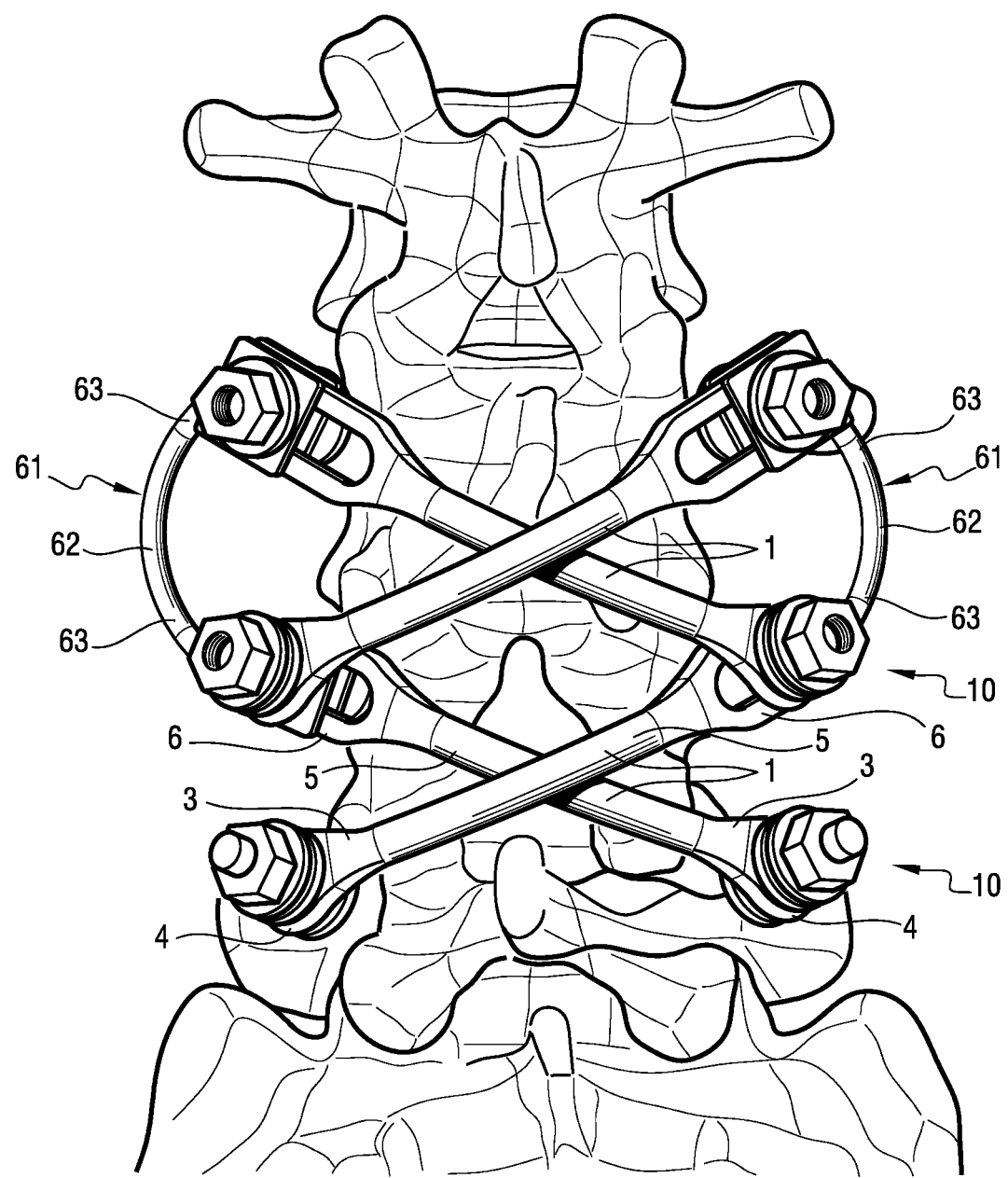
FIG. 21 is a schematic perspective view of the posterior part of the spine equipped with vertebral stabilization devices according to the first embodiment, in a second arrangement of the device.
Figure 22:
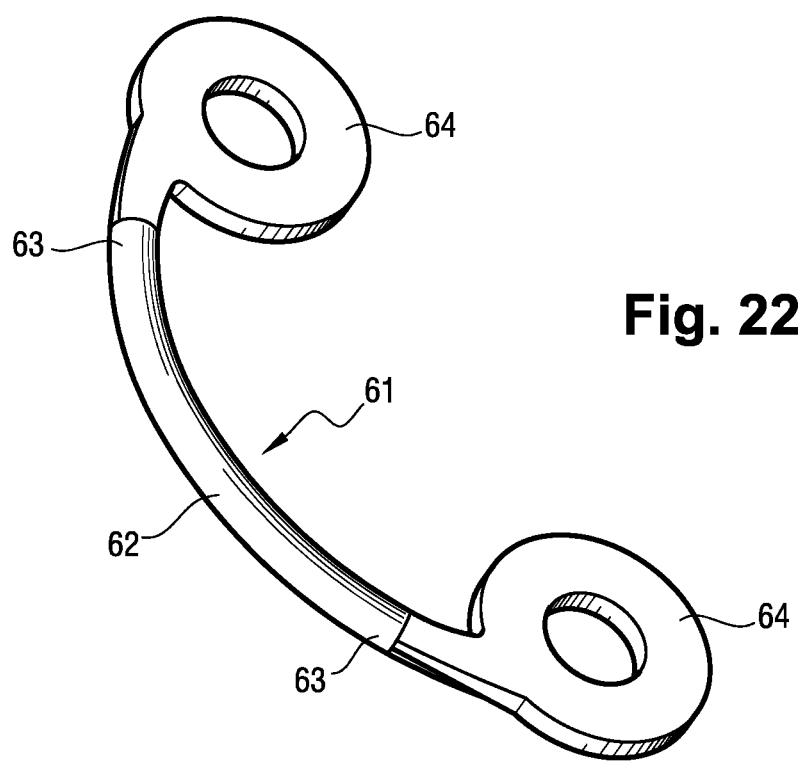
FIG. 22 is an enlarged view of a lateral linking element in the second arrangement of the device.

The elements identical or similar to those described above will bear an identical reference number in the following description of the second embodiment with reference to FIGS. 12 to 14, the third embodiment with reference to FIG. 20, and the second arrangement with reference to FIGS. 21 and 22.

According to the second embodiment, the rods 1a, 1b each have a curved central portion 2, an end portion 3, and an end portion 5. The end portions 3 and 5 are here of constant cross section and are without a ring or loop.

Each attachment element 10 comprises a peg and a nut 41 with a base 42, identical to that of the first embodiment.

The attachment element 10 additionally comprises a body 50 or two bodies 50 depending on whether the attachment element 10 is used to fix one rod or two rods 1.

The body 50 comprises a tubular portion 51, which defines a seat 52 open along its entire length via a slit 53. From the edges of the slit 53 there extend two plates 54, which are parallel to each other and are separated from each other by a space with a width equal to that of the slit 53. The plates 54 have a hole 55 passing through them and are deformed in order to present a slightly frustoconical shape. The seat 52 has a diameter corresponding substantially to that of the end portions 3, 5, and the hole 55 has a diameter slightly larger than the diameter of the threaded rod 40.

One of the bodies 50, labeled 50a, is intended to fix the rod 1a, and the other of the bodies 50, labeled 50b, is intended to fix the rod 1b. The diameter of the hole 55 of the body 50a is greater than that of the hole 55 of the body 50b.

The placement of the stabilization devices will now be described.

As before, the pegs of the attachment elements 10 are fitted in place in the vertebrae concerned.

A body 50a is engaged on one of the threaded rods 40 mounted on vertebra L5, a body 50b is engaged on the other of the threaded rods 40 mounted on vertebra L5, a body 50a and a body 50b are engaged on each of the threaded rods 40 mounted on vertebra L4, a body 50a is engaged on one of the threaded rods 40 mounted on vertebra L3, a body 50b is engaged on the other of the threaded rods 40 mounted on vertebra L3 in such a way that, on one side of the median sagittal plane S, two bodies 50a are mounted on vertebrae L5 and L3, and, on the other side of the median sagittal plane S, two bodies 50b are mounted on vertebrae L5 and L3.

The ends of the rods 1a, 1b are then engaged in the bodies 50a, 50b in such a way that each rod 1 extends diagonally between two adjacent vertebrae, intersecting the median sagittal plane S of the vertebral column, the two rods 1 of each pair of rods 1 intersecting substantially at said plane S. The rods 1a are disposed between the vertebral column and the rods 1b.

It will be noted that the bodies 50 are able to be oriented around the threaded rods 40, which permits adjustment of an orientation of the two rods 1 relative to the same vertebra.

The nuts 41 are mounted on the threaded rods 40, and it is necessary to tighten the nuts 41 mounted on the threaded rods 40 in order to complete the placement of the stabilization device.

To ensure that the rods 1 are tensioned after tightening, use is made of tools having two sheaths arranged to engage on the threaded rods 40 and connected to each other by an adjustable frame, making it possible to space the sheaths apart from each other to a greater or lesser extent.

Once the spacing has been adjusted for fixing a rod 1, the nut 41 is tightened in order to block the attachment element 10 in position on the pedicle screw 30 and the end portions 3, 5 in the attachment element 10. The nut 41 will move the plates 54 toward each other and clamp the end portion 3, 5 in the seat 52, and the attachment element 10 against the shouldered segment 20 connecting the pedicle screw 30 to the threaded rod 40.

It will be noted that, according to the first arrangement of the device, the attachment elements 10 situated on the same side of the median sagittal plane are free with respect to each other.

The rods 1 have mechanical properties allowing them to support forces of compression, traction, flexion and torsion, of the kind that normally occur during natural mobilization of the vertebral column.

Figure 20:
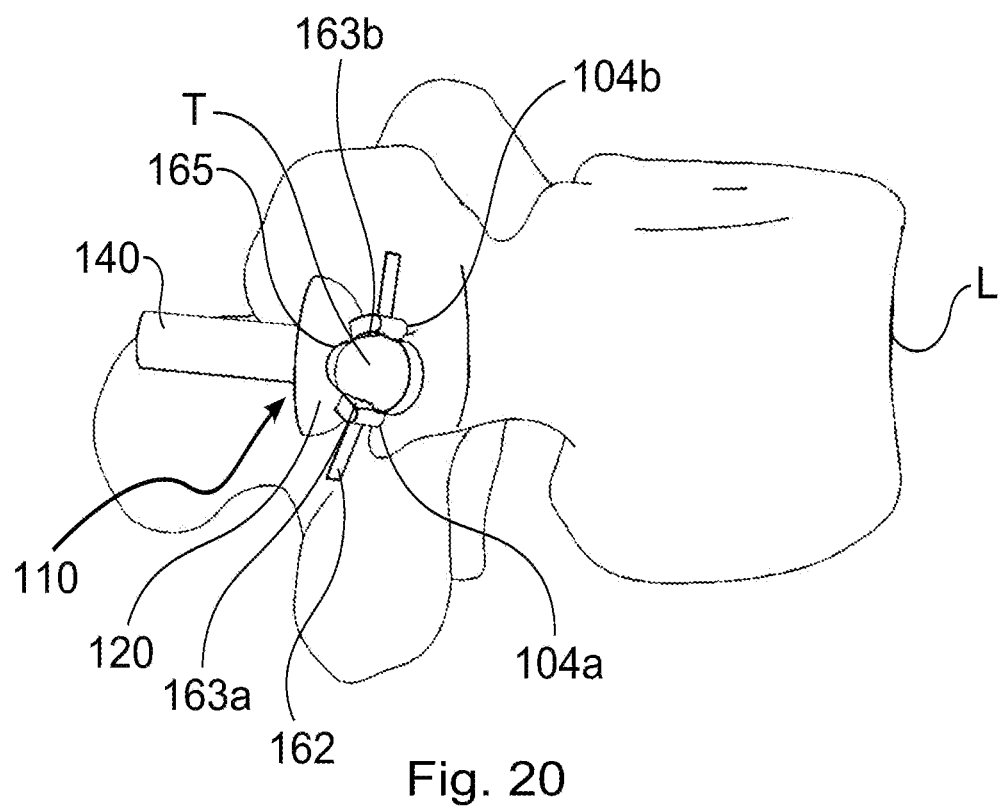
FIG. 20 is a schematic perspective view of a vertebra equipped with an attachment element of a vertebral stabilization device according to a third embodiment of the invention.

The third embodiment, illustrated in FIG. 20, differs from the first embodiment in terms of the attachment elements.

Thus, instead of a pedicle screw, each attachment element 110 here has a lacing cord 162 for securing it to the associated vertebra L. Each lacing cord 162 here is flat.

Each attachment element 110 thus comprises a peg having a shouldered segment 120 continued by a threaded rod 140.

The threaded rod 140 is intended to cooperate with a nut with base (not visible here) as in the first embodiment.

The shouldered segment 120 comprises a first, spherical-cap-shaped surface toward the lacing cord, and a second, truncated surface toward the threaded rod 140. The first, spherical-cap-shaped surface is intended to be oriented toward a transverse process T of the vertebra L. The first, spherical-cap-shaped surface is continued by two ring segments 104a, 104b.

Preferably, in order to press the attachment element 110 optimally onto the transverse process T, the shouldered segment 120 has, at its first, spherical-cap-shaped surface, a trough 165 intended to match the shape of the transverse process T once the shouldered segment 120 is in contact with said transverse process T. The trough 165 has, for example, a semicircular cross section.

Furthermore, the two ring segments 104a, 104b are here configured in the form of an arc of a circle. Each ring segment 104a, 104b extends out from the first, spherical-cap-shaped surface in such a way that the two ring segments 104a, 104b have the same axial direction. The ring segments 104a, 104b are thus oriented in such a way that their radial direction extends substantially perpendicularly with respect to the axis of the threaded rod 140.

Each ring segment 104a, 104b extends on either side, respectively, of the trough 165. Each ring segment 104a, 104b extends in such a way that the internal main surface of each ring segment 104a, 104b is intended to be oriented toward the transverse process T of the vertebra L. It will be noted that the ring segment in the shape of an arc of a circle is adapted to press the attachment element 110 optimally to the transverse process T. Each ring segment 104a, 104b is moreover provided with a groove 163a, 163b, respectively, passing radially through the associated ring segment for passage of the lacing cord 162. The two grooves each extend substantially in the region of the free circumferential end of the associated ring segment (as opposed to the circumferential end of each ring segment integral with the first, spherical-cap-shaped surface).

Thus, in order to fit the attachment element 110 in place, the lacing cord 162 has to be passed through the two grooves 163a, 163b, such that the lacing cord 162, the two ring segments 104a, 104b and the trough 165 thus jointly form a fastening collar.

The collar will then be disposed around the transverse process T.

The lacing cord 162 is then clamped around the transverse process T in order to ensure, by tightening, that the attachment element is fixed to the vertebra L.

The second arrangement of the device will now be described with reference to FIGS. 21 and 22.

The device comprises, as before, rods 1 forming the main linking elements, and attachment elements 10. The rods 1 and the attachment elements can be in accordance with any of the embodiments described above.

The second arrangement is characterized in that the device comprises, on each side of the sagittal plane S, a rod 61 forming a lateral linking element that connects two attachment elements 10 to each other on a same side of the sagittal plane S.

Each rod 61 comprises a central segment 62 having a curvature, and two ends 63 provided in each case with a ring 64 to be engaged on a threaded rod 40. Each rod 61 has a longitudinal axis contained in a particular plane substantially parallel to the median front plane of the vertebral column. Depending on the disease in question, each rod 61 is configured in such a way that the center of curvature of the central segment 62 is in said particular plane, to the side of the sagittal plane S in which the rod 61 in question is located, or in said particular plane, to the opposite side of the sagittal plane S in which the rod 61 in question is located.

Each rod 61 is arranged to be deformable by flexion, accentuating the curvature of the central segment 62.

Each rod 61 mounted between two attachment elements 10 allows the attachment elements 10 connected by it to move toward each other, and it limits a spacing apart of said attachment elements 10 to a distance equal to the length of the rod 61 (the length of the rod 61 here being the actual length of the rod 61, that is to say the length along the curvature of the rod).

In all cases, the material, the shape and the cross section of the rods 1, 61 will be chosen such that the vertebral stabilization device has mechanical and dynamic properties similar to the tensor system (formed by the muscles, aponeuroses and ligaments) that surrounds the osseous structure of the vertebral column.

Of course, the invention is not limited to the embodiments described, and instead it encompasses any variant falling within the scope of the invention as defined by the claims.

In particular, the device can have a structure different than that shown in the figures.

The attachment elements can directly comprise a complete collar arranged to be disposed around a transverse process, in order to fix there an end of at least one rod, instead of a collar formed of several elements, for example as described in the third embodiment.

The attachment elements can be arranged so as to fix just one rod.

Although the attachment elements have been described as being in the form of a rod, they can have other forms, The linking elements can be made of a material other than an organic material, for example of a metal such as titanium.

In one variant, the rods comprise an end portion provided with a ring and a straight end portion, and the attachment elements comprise a body of parallelepipedal shape which is slit along a plane and is provided with two seats for receiving, respectively, the straight end portion and the ring of two rods 1. The seats pass right through along two parallel axes contained in the plane P and corresponding to the direction in which the straight end portion and the ring are introduced into the seats. The seat receiving the straight end portion is of cylindrical shape, and the body is provided with means for clamping the straight end portion in said seat. The clamping means comprise a locking screw engaged in an internal screw thread formed in the body transversely with respect to said seat and having an end opening out into the seat and an end opening out to the outside of the body. The seat receiving the ring is of parallelepipedal shape in order to receive the ring flat and perpendicular to the pedicle screw 30. A bore passes through the body at the seat in order to receive the threaded rod 40.

The two end portions of each rod 1 can be provided with a ring 4.

It is of course possible for different types of embodiments and variants described in the present description to be combined in the same vertebral stabilization device according to the invention. For example, it is thus possible to use, in one and the same vertebral stabilization device according to the invention, attachment elements such as those illustrated in FIG. 1 and likewise attachment elements such as those illustrated in FIG. 20.

It will be possible to use different attachment elements (of the same structure or of different structure) in order to fix the same end of a linking element to the vertebra in question, particularly in the case of a vertebra having a poor quality of bone.

The vertebral stabilization device can have one or more additional linking members (in addition to the linking elements), for example a brace, which are connected to the vertebrae either by way of the attachment elements of said linking elements or by way of other attachment members.

The vertebral stabilization device can be arranged at the posterior aspect and also at the anterior aspect of the vertebral column.

The invention claimed is:

1. A vertebral stabilization device, comprising at least two main linking elements arranged to connect to each other two separate vertebrae of a vertebral column, and attachment elements for attaching ends of each linking element to the two separate vertebrae, characterized in that each main linking element has a median plane containing a longitudinal direction of the main linking element, in that the main linking elements are of such a length, and the attachment elements are so arranged, that each main linking element can extend diagonally between the two vertebrae to which it is attached, intersecting a median sagittal plane of the vertebral column, the main linking elements intersecting substantially at said median sagittal plane of the vertebral column, and in that the device is arranged to permit a physiological angular clearance of the two vertebrae with respect to each other in flexion in the median sagittal plane and in lateral inclination a median frontal plane of the vertebral column, and in torsion around a spinal axis.

2. The device as claimed in claim 1, comprising two lateral linking elements arranged to be positioned one on each side of the median sagittal plane and that connect two attachment elements to each other, each lateral linking element being arranged to allow the attachment elements connected by it to move toward each other, and to limit a spacing apart of said attachment elements to a distance equal to a length of the lateral linking element.

3. The device as claimed in claim 2, in which each lateral linking element is arranged to be deformable in flexion.

4. The device as claimed in claim 3, in which each lateral linking element is a rod having a curvature.

5. The device as claimed in claim 4, in which a center of curvature of the rod is to a side of the sagittal plane.

6. The device as claimed in claim 1, in which at least the attachment elements situated on a same side of the median sagittal plane of the vertebral column and on separate vertebrae are free with respect to each other.

7. The device as claimed in claim 1, in which the main linking elements are positioned with respect to the attachment elements in such a way that each main linking element, and screws of an associated attachment element, extend substantially in a same plane.

8. The device as claimed in claim 1, in which the main linking elements have a curved shape.

9. The device as claimed in claim 8, in which the main linking elements intersecting each other have different radii of curvature.

10. The device as claimed in claim 1, in which the main linking elements have at least one end provided with a ring, which is arranged to be engaged on a stub of one of the attachment elements.

11. The device as claimed in claim 1, in which at least some of the main attachment elements comprise means for clamping a portion of a linking element.

12. The device as claimed in claim 11, in which each attachment element (10; 110) comprises a peg having a shouldered segment (20; 120) and a threaded rod (40; 140), the threaded rod (40; 140) being intended to cooperate with a nut (41) for clamping a portion of a linking element.

13. The device as claimed in claim 12, in which at least one of the attachment elements (10) comprises a pedicle screw (30), which is coaxial to the threaded rod (40).

14. The device as claimed in claim 12, in which at least one of the attachment elements (110) comprises a lacing cord (162).

15. The device as claimed in claim 11, in which the attachment elements are arranged to permit an adjustment of relative positions of the linking elements.

16. The device as claimed in claim 1, in which each attachment element comprises a pedicle screw.

17. The device as claimed in claim 1, in which at least two of the attachment elements are arranged to attach two linking elements to the same vertebra.

18. The device as claimed in claim 17, in which said attachment elements are arranged to permit an adjustment of an orientation of the two linking elements with respect to the same vertebra.

19. The device as claimed in claim 1, in which the linking elements are made of organic material.

20. The device as claimed in claim 19, in which the organic material is a composite material incorporating reinforcement fibers.

* * * * *